United States Patent
Tucker et al.

(10) Patent No.: US 11,673,321 B1
(45) Date of Patent: Jun. 13, 2023

(54) CUSHIONED PRODUCT MADE USING ADDITIVE MANUFACTURE

(71) Applicant: EOS of North America, Inc., Novi, MI (US)

(72) Inventors: Joseph Tucker, Pflugerville, TX (US); Paul South, Pflugerville, TX (US); Donald Vanelli, Pflugerville, TX (US)

(73) Assignee: EOS of North America, Inc., Novi, MI (US)

( * ) Notice: Subject to any disclaimer, the term of this patent is extended or adjusted under 35 U.S.C. 154(b) by 230 days.

(21) Appl. No.: 17/014,290

(22) Filed: Sep. 8, 2020

Related U.S. Application Data

(60) Provisional application No. 62/897,619, filed on Sep. 9, 2019.

(51) Int. Cl.
| | |
|---|---|
| *B29C 64/153* | (2017.01) |
| *B33Y 10/00* | (2015.01) |
| *B29C 64/393* | (2017.01) |
| *B33Y 80/00* | (2015.01) |
| *B33Y 50/02* | (2015.01) |
| *B29L 31/50* | (2006.01) |
| *A61B 5/103* | (2006.01) |
| *A61F 5/14* | (2022.01) |

(52) U.S. Cl.
CPC .......... *B29C 64/153* (2017.08); *B29C 64/393* (2017.08); *B33Y 10/00* (2014.12); *B33Y 50/02* (2014.12); *B33Y 80/00* (2014.12); *A61B 5/1036* (2013.01); *A61F 5/14* (2013.01); *B29L 2031/50* (2013.01)

(58) Field of Classification Search
CPC ..... A61B 5/103; A61B 5/1036; A61B 5/1038; B29L 2031/50; B29L 2031/501; B29L 2031/502; B29L 2031/504; B29L 2031/507; B29C 64/386; B29C 64/393; B29C 64/153
See application file for complete search history.

(56) References Cited

U.S. PATENT DOCUMENTS

| | | | |
|---|---|---|---|
| 2016/0052087 A1* | 2/2016 | O'Neill | B22F 10/366 219/76.12 |
| 2020/0060580 A1* | 2/2020 | Miller | A61B 5/1074 |

\* cited by examiner

*Primary Examiner* — Joseph S Del Sole
*Assistant Examiner* — Jamel M Nelson
(74) *Attorney, Agent, or Firm* — Seyfarth Shaw LLP

(57) ABSTRACT

A method for making an article for application to the human body. Data from measurement of pressures across an area of a person's body is obtained, which is then corresponded to a two-dimensional pressure map of a model of an article for application to that body area and identifying pressure-point locations and a pressure value for identified pressure-point location within the pressure map. Each different pressure value has a compression unit structure corresponding to that pressure value. The article is formed by generating the assigned respective structures in an integrated one-piece construct through layerwise build up in an additive manufacture system, where the build up includes a process that forms a joinder in an interface between adjacent contiguous structures which differ in geometry from one another so as to bond those contiguous structures together across the interface.

4 Claims, 15 Drawing Sheets

| NAME | PICTURE | STRUCTURE DIMENSION | CELL DIMENSION | EXPOSURE | SHORE HARDNESS (ASKER C) | ASTM D395 COMPRESSION SET AVG% |
|---|---|---|---|---|---|---|
| BLK_F/M/H | 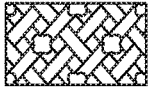 | 5X5X5 | F: 10x10x5<br>M: 10x10x7.5<br>H: 10x10x9 | _BLK(F,M,H) | 55-60 | 3%-6% |
| BLU_F/M/H | 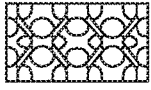 | 10X10X5 | F: 10x10x5<br>M: 10x10x7.5<br>H: 10x10x9 | _BLU(F,M,H) | 50-55 | 5%-7% |
| GRN_F/M/H | 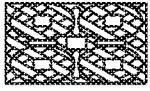 | 10X10X5 | F: 10x10x5<br>M: 10x10x7.5<br>H: 10x10x9 | _GRN(F,M,H) | 45-50 | 4% |
| YEL_F |  | 10X10X5 | F: 10x10x5 | _YELF | 40-45 | 4%-6% |
| ORG_F/M/H | 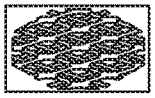 | 2.5X2.5X5 | F: 10x10x5<br>M: 10x10x7.5<br>H: 10x10x9 | _ORG(F,M,H) | 35-40 | 4%-7% |
| RED_F |  | 2.5X2.5X5 | F: 10x10x5 | _REDF | 35-40 | 4%-7% |
| YEL_M/H | 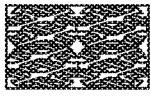 | 2.5X2.5X5 | M: 10x10x7.5<br>10x10x9 | _YEL(M,H) | 40-45 | 4%-7% |
| RED_M/H |  | 2.5X2.5X5 | M: 10x10x7.5<br>10x10x9 | _RED(M,H) | 35-40 | 4%-7% |
FIG. 9

Output 18 structure .stl file to folder
[e-QNAP1] (X:) GEN 1 PRODUCTION ONLY > STEP3 Output from Sia _CU05EM120RB

| Name | Date modified | Type | Size |
|---|---|---|---|
| 0MEU32GlennStrickman_CU05EM120R... | 4/23/2019 11:38 AM | STL Document | 10,284 KB |
| 0MEU32GlennStrickman_CU05EM120R... | 4/23/2019 11:38 AM | STL Document | 18,528 KB |
| 0MEU32GlennStrickman_CU05EM120R... | 4/23/2019 11:38 AM | STL Document | 42,334 KB |
| 0MEU32GlennStrickman_CU05EM120R... | 4/23/2019 11:38 AM | STL Document | 4,943 KB |
| 0MEU32GlennStrickman_CU05EM120R... | 4/23/2019 11:38 AM | STL Document | 7,273 KB |
| 0MEU32GlennStrickman_CU05EM120R... | 4/23/2019 11:38 AM | STL Document | 32,427 KB |
| 0MEU32GlennStrickman_CU05EM120R... | 4/23/2019 11:38 AM | STL Document | 2,386 KB |
| 0MEU32GlennStrickman_CU05EM120R... | 4/23/2019 11:38 AM | STL Document | 6,404 KB |
| 0MEU32GlennStrickman_CU05EM120R... | 4/23/2019 11:38 AM | STL Document | 2,366 KB |
| 0MEU32GlennStrickman_CU05EM120R... | 4/23/2019 11:38 AM | STL Document | 5,386 KB |
| 0MEU32GlennStrickman_CU05EM120R... | 4/23/2019 11:38 AM | STL Document | 1,341 KB |
| 0MEU32GlennStrickman_CU05EM120R... | 4/23/2019 11:38 AM | STL Document | 1 KB |
| 0MEU32GlennStrickman_CU05EM120R... | 4/23/2019 11:38 AM | STL Document | 2,486 KB |
| 0MEU32GlennStrickman_CU05EM120R... | 4/23/2019 11:38 AM | STL Document | 31,076 KB |
| 0MEU32GlennStrickman_CU05EM120R... | 4/23/2019 11:38 AM | STL Document | 1 KB |
| 0MEU32GlennStrickman_CU05EM120R... | 4/23/2019 11:38 AM | STL Document | 9,001 KB |
| 0MEU32GlennStrickman_CU05EM120R... | 4/23/2019 11:38 AM | STL Document | 12,753 KB |
| 0MEU32GlennStrickman_CU05EM120R... | 4/23/2019 11:38 AM | STL Document | 3,915 KB |

FIG. 14

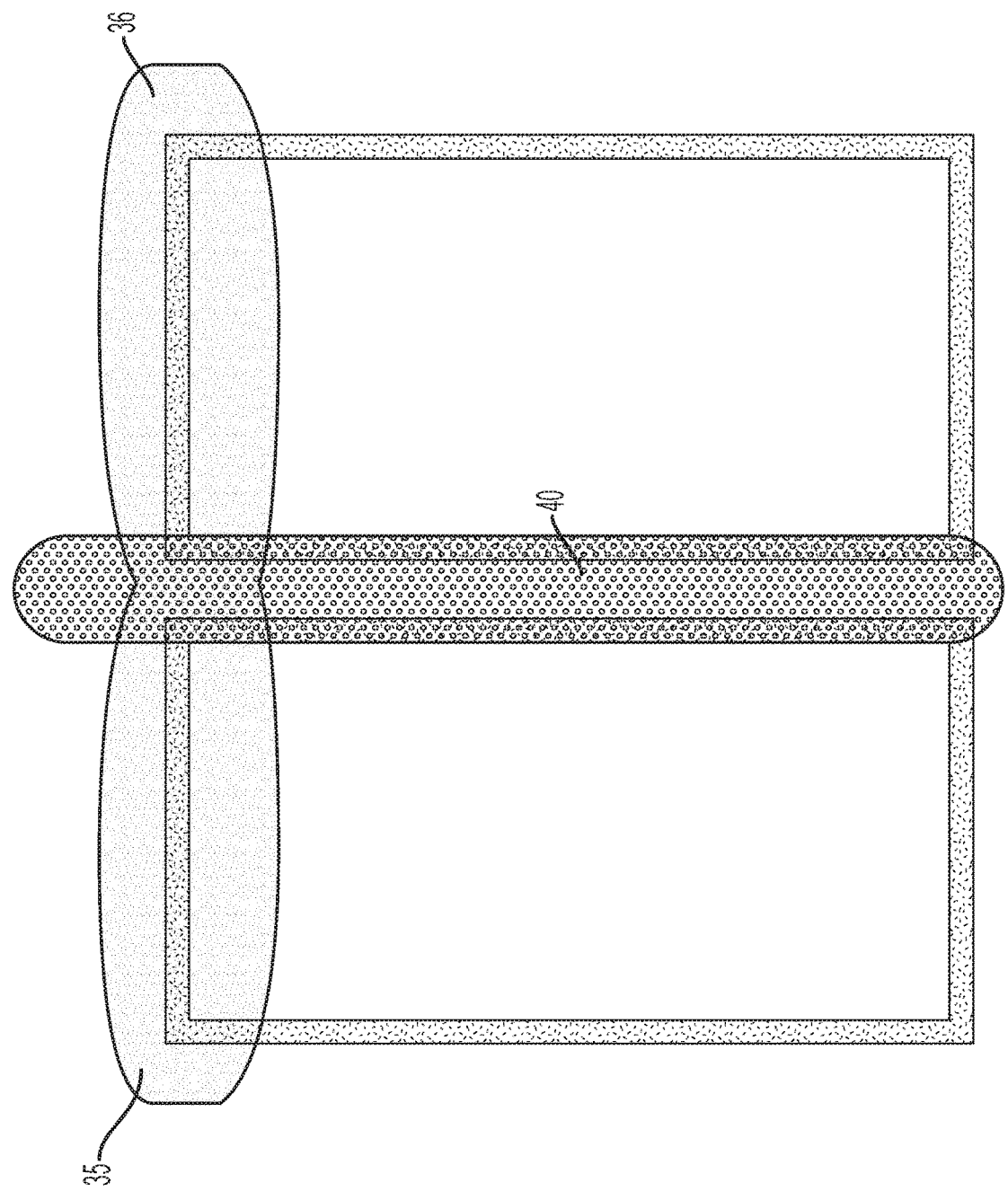

CUSHIONED PRODUCT MADE USING ADDITIVE MANUFACTURE

CROSS-REFERENCE TO RELATED APPLICATIONS

The present application claims priority to U.S. Patent Application Ser. No. 62/897,619, the contents of which are hereby incorporated by reference in their entirety.

BACKGROUND OF THE DISCLOSURE

The invention relates to a system of defining, generating, organizing and integrating in an orthotic or like device, as in footwear, individual cushioning CAD models, specifically designed for the laser sintering (e.g., energetic fusion of a fluent material) process, engineered to work together to achieve a specific spring response, compression set, and Asker C shore hardness system based on a controlled energy input from the laser or other energy beam source. Based on the pressure reading from the scanner, a specific model and energy can be selected to achieve the desired spring/cushion response. This has required a combination of design engineering and system parameter development to create a fully customizable cushioning product.

Note further that while described as cushioning, the invention is of broader yet related scope. Some kind of response to a sensed pressure being applied by an area of a body could be cushioning, as well as resilient resistance of some sort, flexation, absorption or dissipation of force, and so forth.

The present application continues the development of the disclosure of U.S. Ser. No. 15/896,999, filed Feb. 14, 2018, the contents of which are herein incorporated by reference.

The invention has found particular application as an orthotic insert in footwear. Its application is of course much broader than that. In a present embodiment, it is a type of orthotic device that, when inserted into a shoe and applied to a foot, supports the foot in a manner which is intended to provide differing but desired responses to pressures that are presented across different parts of the foot, as in walking, running, standing. Indeed, such orthotic inserts may be used to treat biomechanical deformities as well as inflammatory conditions (e.g., plantar fasciitis). Or simply to make a more comfortable fit.

Some typical current methods of orthotic insert manufacture are directed to molded orthotic inserts. These tend to be generic and not at all custom. Some methods use machining of hard materials, in what is termed a subtractive approach. There have also been products that reduce pressure by modifying a removable orthotic or insole that fits inside a shoe by removing selected pieces of the orthotic or insole. This also limits the range of characteristics (flexibility, shock absorption, weight, etc.) of the end product. Shapes of the orthotic inserts may be somewhat haphazard when based upon limited physiological input of the particular individual, with the design of the orthotic drawn from generalized information in a database for something that might match that physiology.

Various methods have been employed to produce orthotic inserts. For example, plaster cast, gait scanning, and laser scanning methods attempt to capture plantar geometry in a weight-bearing position. However, such methods are generally slow in acquiring orthotic data, expensive, and limited in the range of characteristics that they can provide to the resulting orthotic device. In such methods, the resulting orthotic device is somewhat customizable insofar as it is designed with a particular result in mind, but still it is implemented as a one (or multiple but limited)-size-fits-all solution that may be far from optimal.

There are known implementations for producing orthotic devices from user-captured data. Image data of a body part of a patient (e.g., the patient's foot) can be captured using a camera. Data can be gathered using a pressure-sensitive interface, such as would gather information of the plantar area with a person standing upon the interface. Data may also be captured during the image/pressure data capture, which may facilitate processing of the resulting orthotic. This may be data entry of patient (user) information, which can include physical parameters related to the patient (e.g., height, weight, body mass index, age, pre-existing medical conditions, wear pat-terns on the patient's shoes, etc.). Relevant representative scanning-type technologies for user-captured data are shown in USPub 2017/228859, and 2016/101572 for example.

The captured image/pressure data, patient information and the like may be transmitted to a server operating an analytic and design program, which will then in turn be used to generate orthotic model data (e.g., CAD data) for an orthotic device (e.g., an orthotic shoe insert). That model data then is translated into an actual orthotic as by input to a layerwise additive manufacturing apparatus that can fabricate an orthotic device from the orthotic model data, colloquially referred to as "3D printing" (AM).

It will be understood that the present invention is not limited to application in just footwear. It can be applied to any number of other constructs that are based upon pressure measurements of an individual's body part, e.g., a foot for an insole, or part of a head for a helmet, an elbow for a pad, a bicycle seat, a space suit, and so on. Nor is the invention limited to the type of AM described hereafter, as it could be implemented through SLA, wherein a liquid polymer is solidified in a vat of material, or other known AM techniques.

It is known to make an orthotic or insole for footwear using a pressure plate, which then senses applied pressure from the foot bottom, and generating a corresponding pressure map of the sole of a foot. This can determine regions of high relative pressure which may indicate that the area is exceeding a predetermined relative pressure level. That then can be translated to an orthotic or insole including an area corresponding to accommodate that sensed pressure in a helpful (comfort) or therapeutic way.

The present invention has again found particular application for the design of such footwear othotics in a much more customizable fashion, where pressure mapping of the foot is used and pressure information from the pressure map is extracted to then create an orthotic using an AM system, wherein the CAD model for the orthotic is adjusted via selectively varying elemental structures and/or material hardness at selected areas of the orthotic to achieve the desired pressure responses to the sensed pressure information, resulting in a now truly custom made orthotic or insole to custom make orthotic shoes or orthotics or insoles for individuals.

SUMMARY OF THE DISCLOSURE

In one form, the inventive method and apparatus use information relating to the pressure applied by the sole of a person's foot by using different structural or elemental components. These structural components can comprise, for example, individual compression cells or units, which have a predetermined geometry so as to produce a known compression-resistance response. The kinds of structural units may be multifarious. Moreover, how those units interact as a whole in horizontal groupings in an area of joined common units, as well as in stacked configuration, is also determined. Pressure readings taken for the foot identify pressure points for that foot. Those pressure points, typically then generalized over an area, are quantified and the foot is "mapped" in a grid format on a pressure map. Once mapped, then the structural units and unit assemblies corresponding to a particular pressure value are matched for a "best fit" to, e.g., respond to the mapped pressure area in a desired way, as by alleviating some overpressure detected. For instance, this may be to unload foot pressure in high pressure areas of the foot at those points.

A significant aspect of the present invention is not only the design and selection of the elemental geometries, both individually and as a common group, but also the selection of contiguous areas of differing kinds of units across the orthotic. Further still, it has been a significant development to adjust the response of a particular unit geometry through the amount of energy that is used to fuse that unit shape. Meaning, a unit can be modified by the amount of heat (laser energy in joules) applied in manufacture of that unit itself. The unit is thus tailorable all unto itself by making it harder or softer, depending upon the energy of fusion (melting).

A still further significant development has been in the integration, or knitting, of the various and differing units across the orthotic. Consider that the edges of the area of one assemblage of structural units in a footsole model have to join with the edges of contiguous but different areas using different structural units for differing pressure responses. There is thus a transition region between areas of one kind of structure-hardness and another. The present invention has surmounted the problem of how to achieve an effective transitional integration for a durable end product. In one embodiment, this is accomplished by using a laser beam (energy beam) having an offset set to zero, whereby an overlap is created between adjacent contiguous areas of differing structural elements.

This results in a CAD model for the orthotic, which is then created as an actual orthotic via AM manufacture, as in a powder bed fusion layerwise build up (sometimes simply referred to as Laser Sintering or SLS). All of this is accomplished in a single integrated single piece orthotic.

These and other aspects of the invention will be further understood and appreciated through the following detailed description of embodiments thereof, taken in conjunction with the drawings in which:

BRIEF DESCRIPTION OF THE DRAWINGS

FIG. 9 sets forth a table correlating the types of structures for an embodiment;

FIGS. 10 through 16 show representative process steps;

FIGS. 17 and 18 schematically illustrate how a problem of joining adjacent areas of differing structural elements was overcome.

DETAILED DESCRIPTION OF EMBODIMENTS

Figure 3:
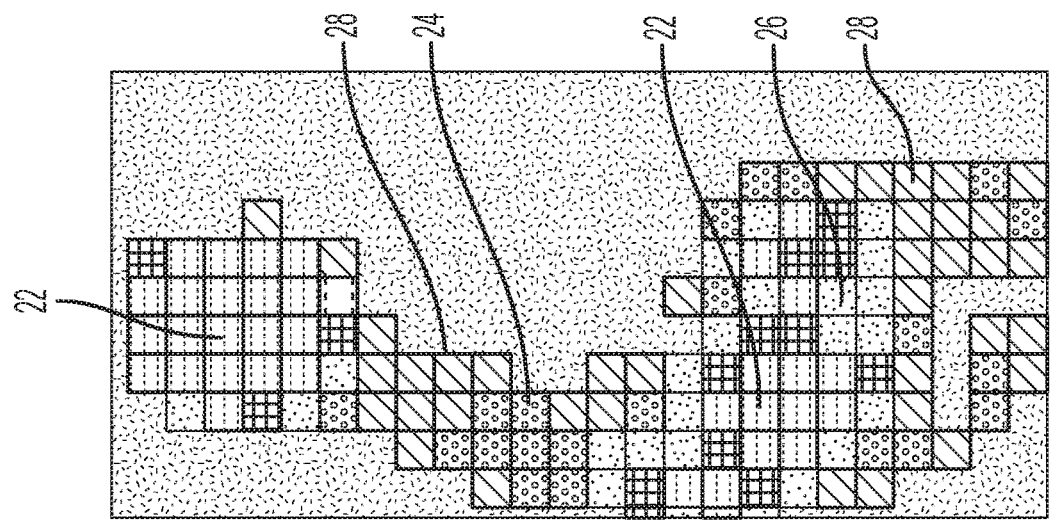
FIG. 3 depicts an iterization where pixel areas are now being defined to correspond to the more generalized iterization of FIG. 2.

As mentioned above, the present invention has found particular application in the design and manufacture of a custom foot orthotic or insole through additive manufacture, such as through powder bed fusion of polymer powder. This type of additive manufacture is colloquially referred to as "3D printing." The present invention, however, is not limited to application in just footwear, as it can be applied to any number of other constructs that are based upon pressure measurements of an individual's body part, e.g., a foot for an insole, or part of a head for a helmet, an elbow for a pad, and so on. Nor is the invention limited to the type of AM described hereafter, as it could be implemented through SLA, wherein a liquid polymer is solidified in a vat of material, or other known AM techniques.

In a preferred embodiment, the pressure measurements are mapped to create a data model of the foot after the individual stands upon an electronic pressure plate that uses pressure sensors and receives a pressure analysis of the foot. This is as described in the aforementioned U.S. Ser. No. 15/896,999, which is incorporated by reference. The invention is not limited to the use of sensor devices of the type shown therein, however, and any manner of obtaining pressure measurements, including but not limited to, thermal pressure measurement devices, or manual methods such as a Harris mat foot imprinter (e.g., methods where data is obtained and manually input to the system) can be used to obtain the pressure measurements and still fall within the scope of the claimed invention.

The data from the sensed or measured pressure is then translated into a model of an insole, which is designed to provide differing amounts of pressure as for unloading appropriate to the foot. This is done by selecting corresponding pressure values associated with a sensed pressure which are then themselves determined for manufacture through selection of individual compression structures or cells which will yield the desired pressure response within he orthotic or insole. That desired pressure response is determined over areas of same structural elements (cells) as well as the selection of contiguous areas of other structural elements, as how differing areas transition one to another can be an important consideration in the final product.

The various structural elements have specific compression characteristics as a basic unit. However, those elements can further be modified at a specific location as to material hardness, material soft-ness, or some other inherent feature by nature of the amount of energy applied in manufacture of the structure in situ. This is a major advantage of this use of AM, as one kind of build material is preferably used in manufacture. While the basic geometry of a structural element is set and the element selected in correspondence to a respective pressure value, that element can nonetheless be further tailored by adjusting the amount of energy applied in the build operation. For instance, using laser fusion or melting as the AM process, that laser output at a location can be adjusted for a nuanced response further desired of the element, as in more hardness or softness within the element itself. So too, the physical shape of the structural element can be "tweaked" in a highly granular manner during the build process.

Figure 1:
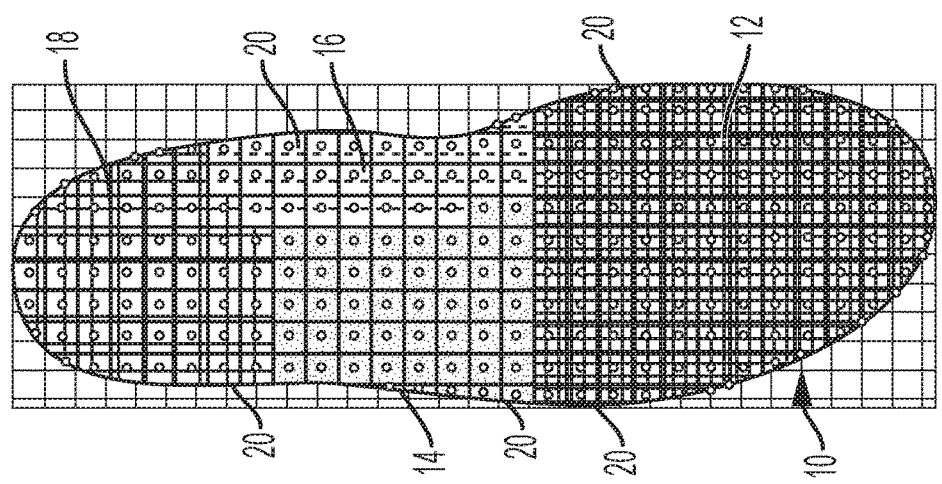
FIG. 1 is a screenshot of a planar representation of a model shoe sole orthotic, showing various generalized regions to be mapped.

Turning now to FIG. 1, what is shown is a generalized computer model of the bottom of an insole 10. As can be seen, the insole model is initially delineated by areas corresponding to the foot forefront 12, midsole 14, arch 16 and heel 18. These areas are further then divided into subregions 20 which will correspond to pixels which will then be employed for locating sensed pressure data on the model. The CAD (computer-aided design) model 10 of an orthotic or insole is thus converted into a grid which may vary in size where each individual grid file corresponds to a pressure sensor. From that matrix, an individual structure at a grid location, or a designated number of different groupings of structures, can be created based on the scan data in point.

Figure 2:
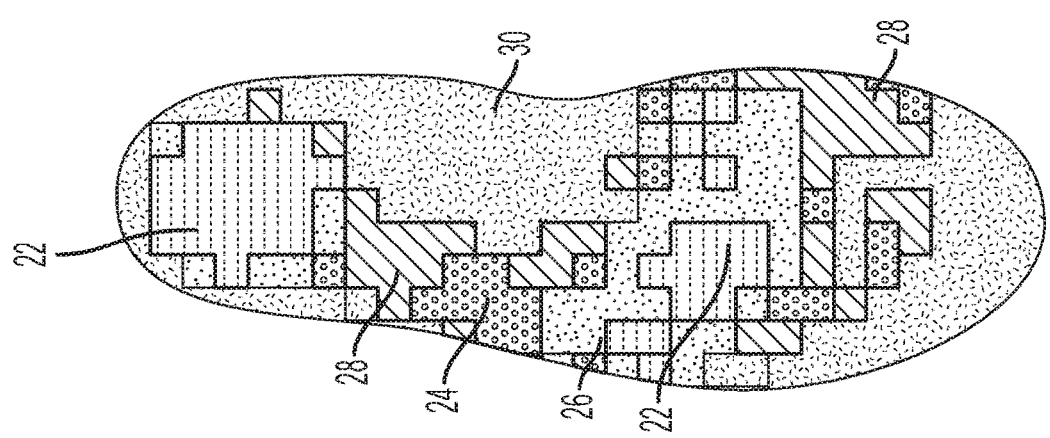
FIG. 2 is an iterization of a scan taken of an actual person's foot along the bottom thereof.

FIG. 2 is a first iterization represented in polychromatic format of foot pressure data of the individual who has been scanned and as collected by the foot scanner. The pressure-point analysis readings from the electronic pressure plate measurements are represented by corresponding colors, where red 22 is the greater pressure, green 24 is lesser pressure, yellow 26 is more pressure than green 24 and blue 28 is less than green 24. Of course, other schemes to represent the pressure readings can be readily utilized, but this type of color-matching has been found to be useful. Black 30 is simply no data or below the threshold of usefulness for this type of orthotic.

FIG. 3 is a further iteration of the generalized pressure data mapping of FIG. 2, now matched to the pixel areas 20.

Figure 4:
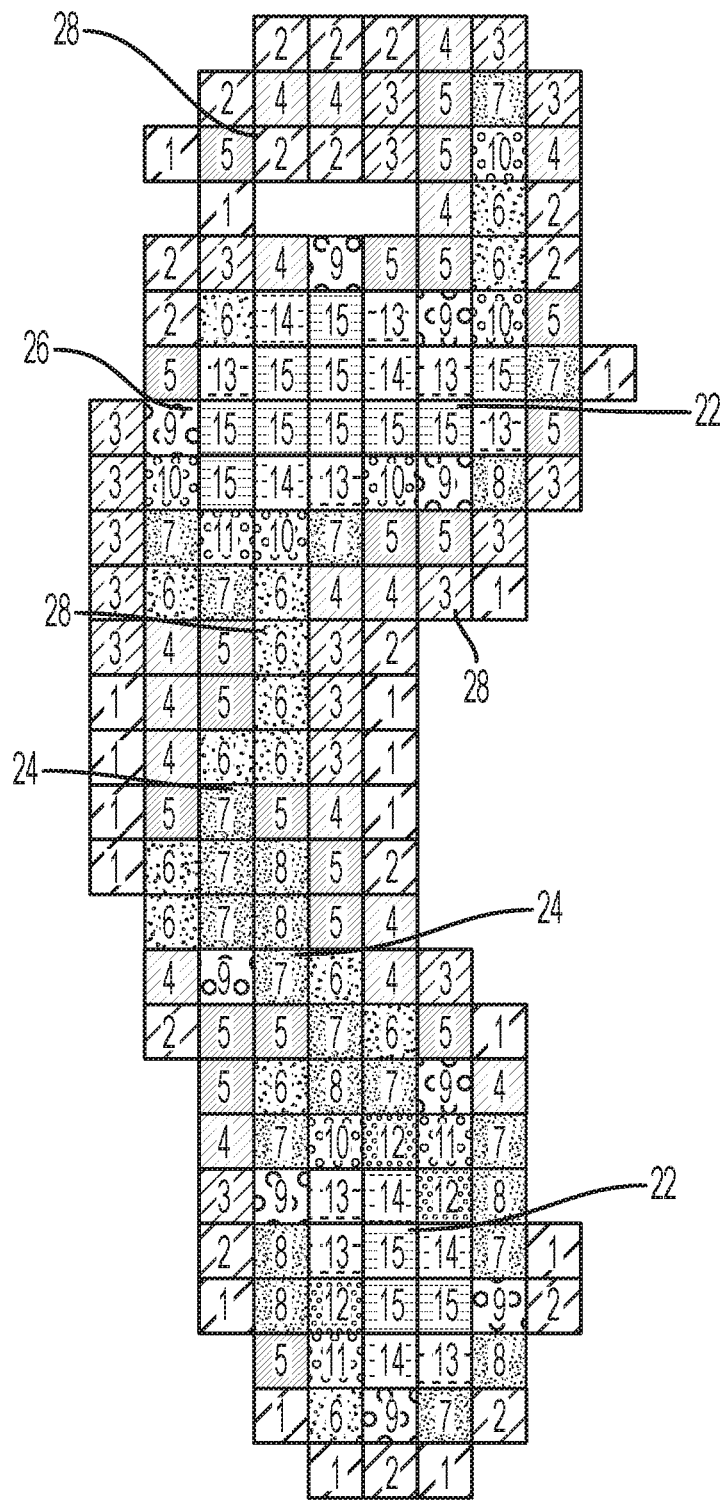
FIG. 4 depicts how values have been assigned to pixels representing pressure points, where the pixel values will correspond to certain structural units matched to the pressure points.

Turning to FIG. 4, this embodiment utilizes a scale of 1 through 15 which correspond to a respective sensed pressure and therefore in correspondence to the structural element which will be then fabricated responding to that pressure reading and its respective pixel. The color scheme shown in FIG. 3 has been further refined to now have gradations within red 22, green 24, yellow 26 and blue 28, each with its value on the foregoing scale. There is nothing magical about the scale, or the pixel size. These were selected here as useful and practical for the purpose.

Figure 5:
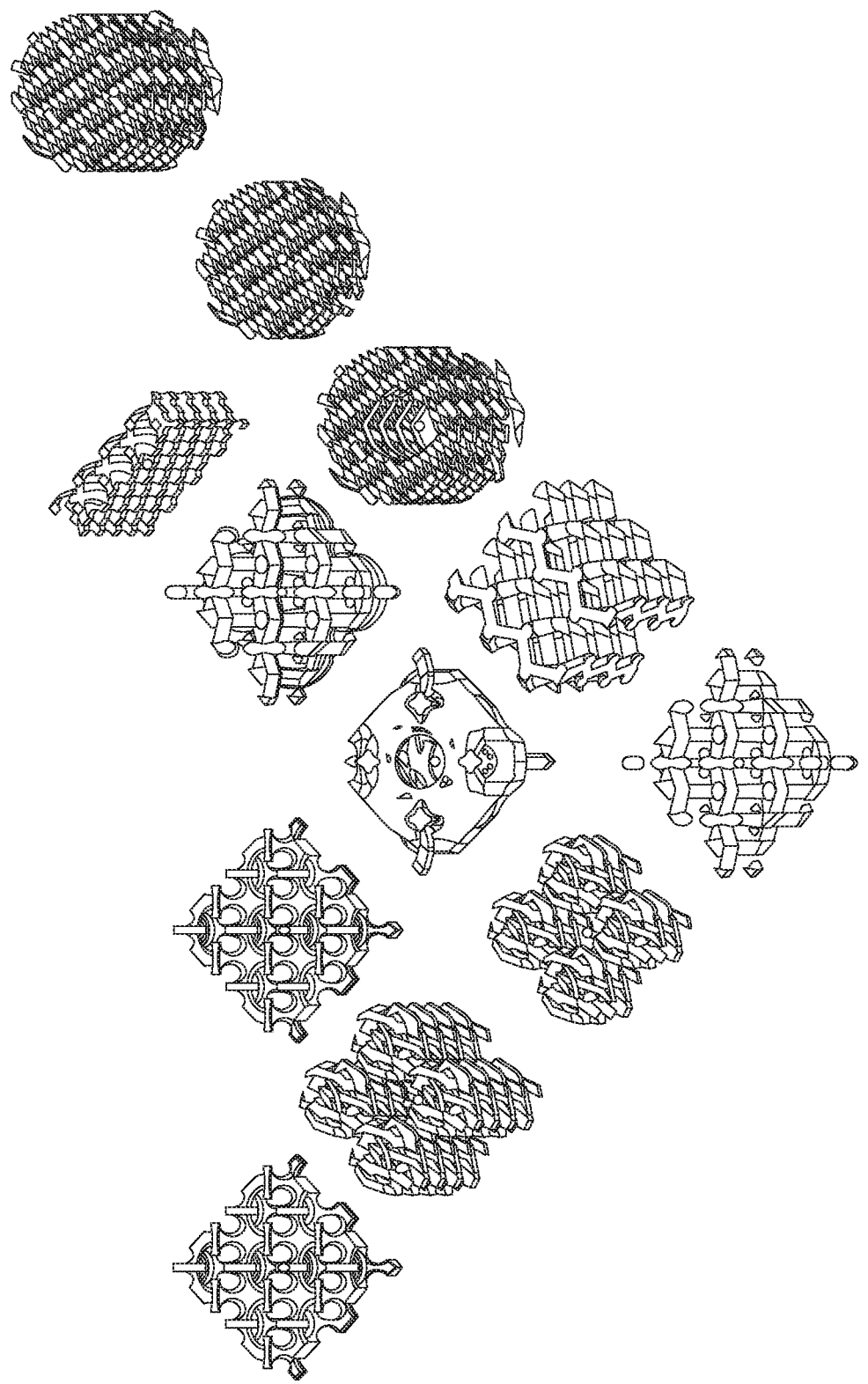
FIG. 5 shows a variety of different structural units which can be fabricated to respectively correspond to certain values associated with pressure points.

A variety of differing structural elements, units or cells if you will, are shown in FIG. 5. The design of these elements in terms of shape, geometry and basic compression and recovery response was determined empirically. A particular type of structural element was then associated with a value on the scale of 1 to 15, so as to provide the pressure value of the finished insole indicated for that number.

FIG. 9 sets forth a table correlating the types of structures and their relative hardness and compression values for one exemplary embodiment. For instance the "color" correlation is set forth in the Name column, Structure Dimension and Cell Dimension columns provides cell size data, Hardness is expressed in Shore Hardness numerology, and an empirically determined Compression Set Avg. as indicated. Note that the Picture representations in FIG. 9 are not to scale, being stretched laterally in these reproductions (the structures actually being symmetric as in FIG. 5).

Figure 6:
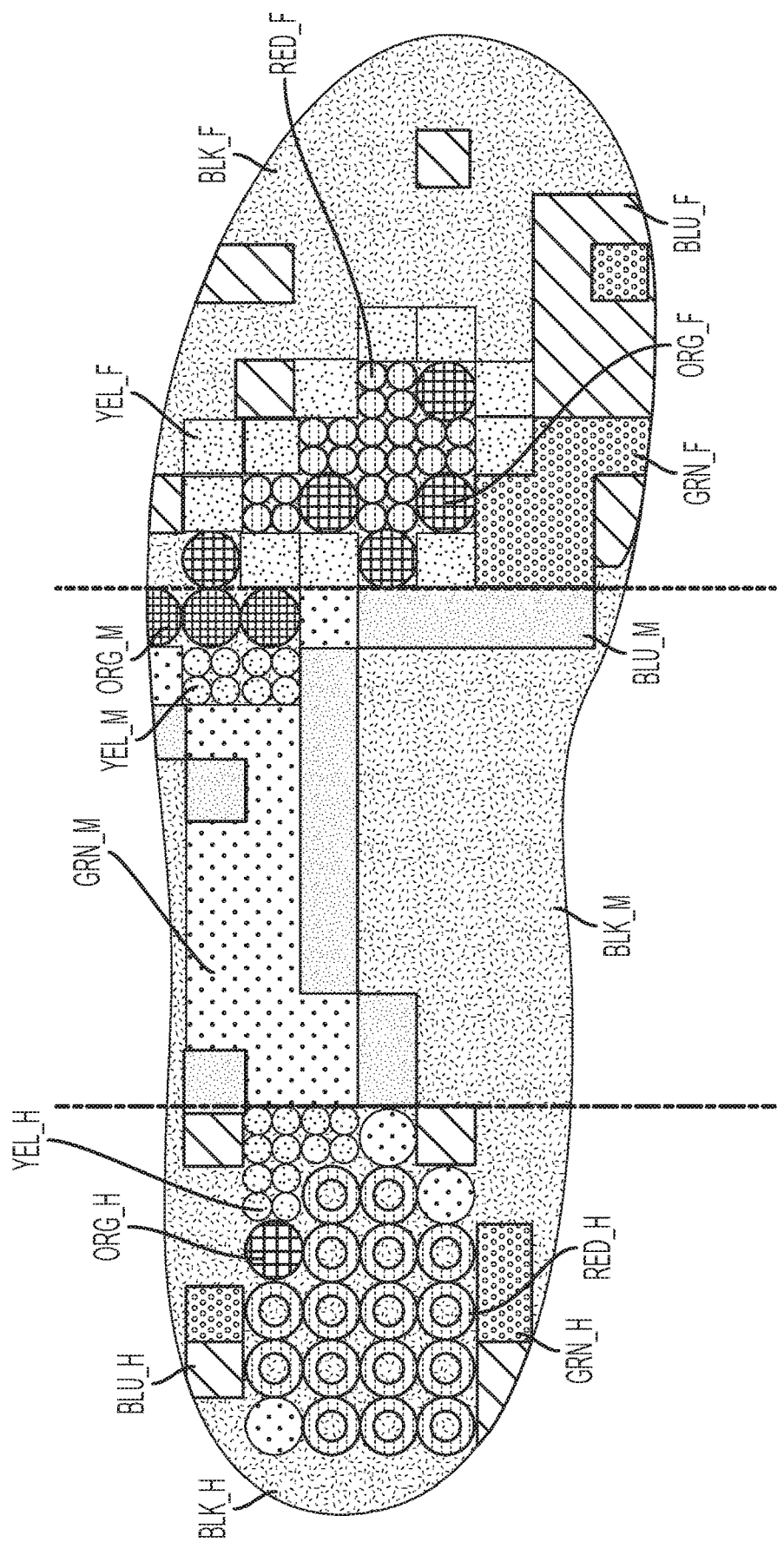
FIG. 6 shows the bottom of an insole with structural units in place corresponding to the certain values associated with pressure points (e.g., of FIG. 4)
Figure 7:
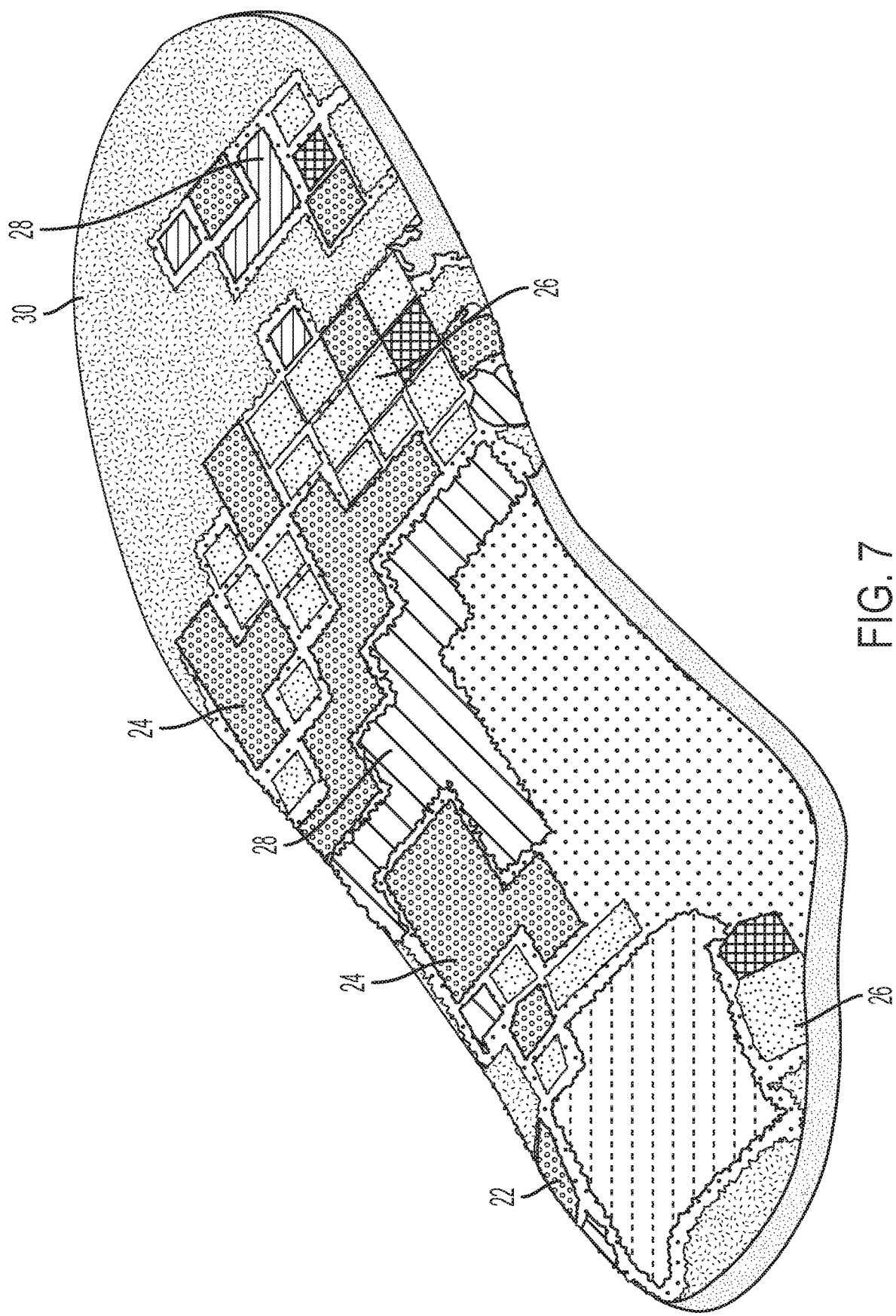
FIG. 7 is a perspective view of the insole of FIG. 6.

FIGS. 6 and 7 then show how these structural elements are organized for a desired insole, keyed to the elements set forth in the table of FIG. 9. An area may contain only one kind of structural element, or multiple kinds so as to yield the desired response in use of the insole. For instance, looking at the front third of the insole in FIG. 6, there is an area of designated red elements, which is surrounded by orange elements and yellow elements, so as to give the desired pressure response of the insole based upon the sensed pressure map data.

One of the challenges of this kind of design is integrating the various contiguous areas of varying hardness/softness. The transition from one to another can be fairly abrupt, and the shear forces thereby experienced across a transition can lead to fractures and separations. To surmount this issue, a program was determined which effectively stitched of knit across these transition regions.

Figure 8:
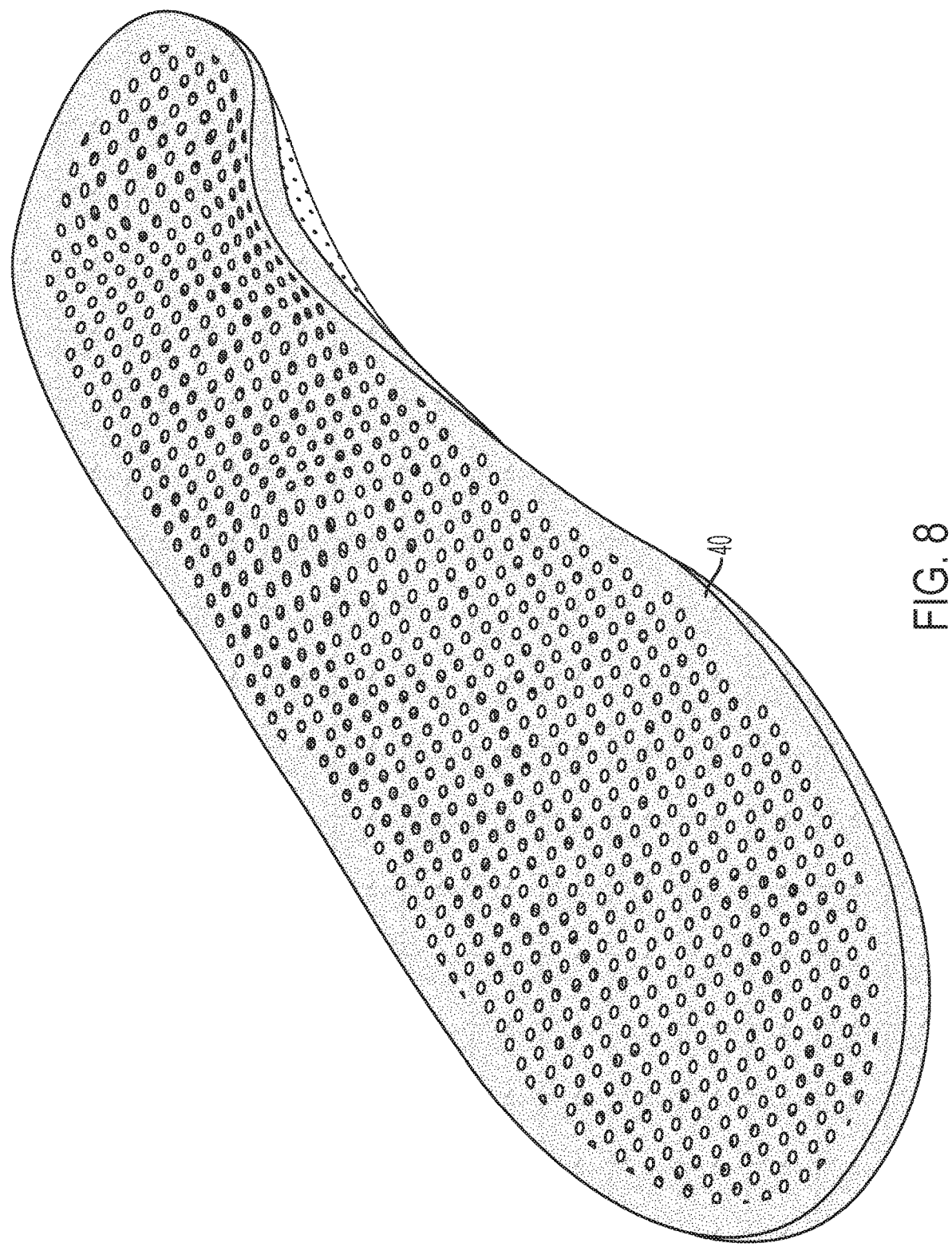
FIG. 8 is a perspective view of the insole of FIG. 7, now with a thin overlayer having been applied across the topside of the insole.

FIG. 7 is a top perspective view of another embodiment of an insole, providing some surface topography. FIG. 8 shows a layer 40 applied over the top of the finished insole, which could be a fabric layer adhered to the insole in a separate step from insole manufacture, or a top layer generated during the AM process.

Figure 10:
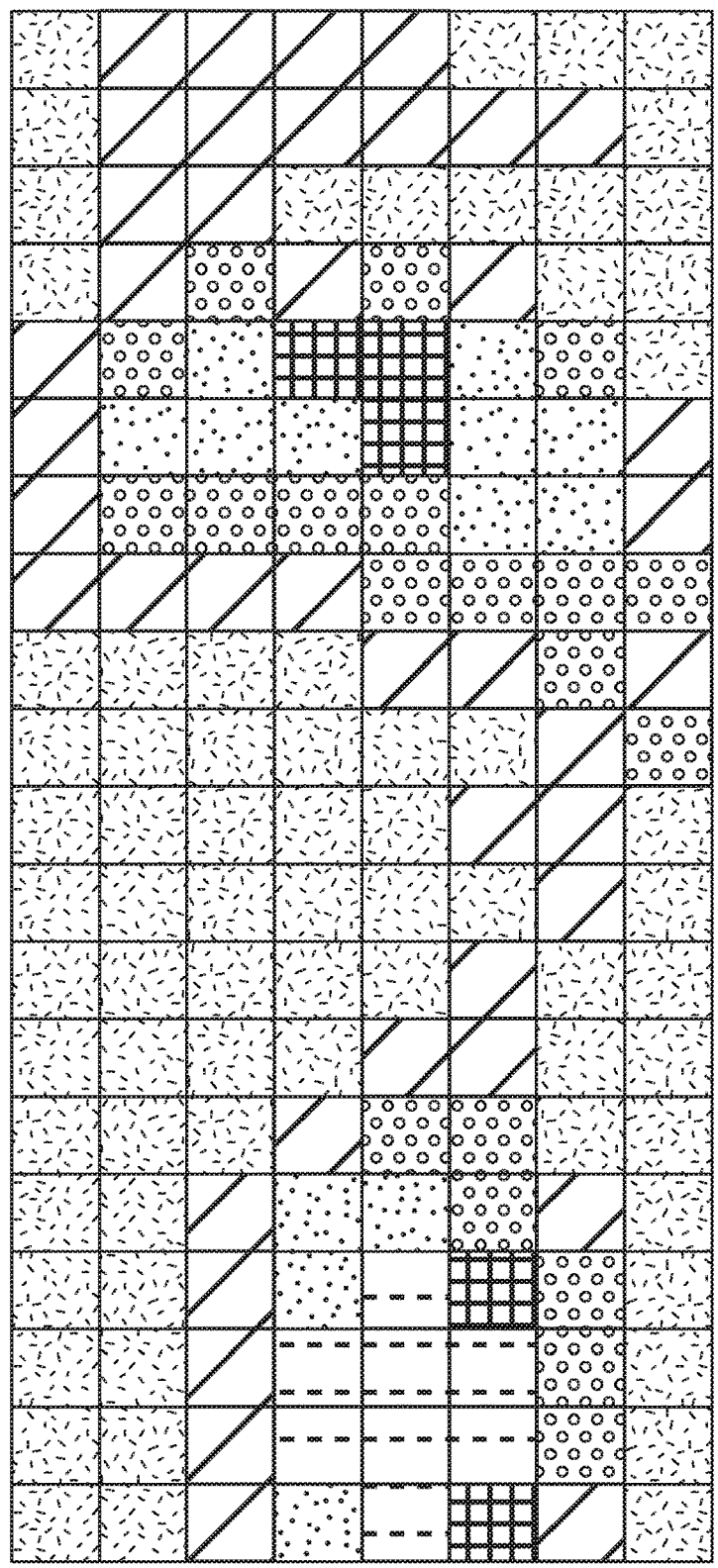
Figure 11:
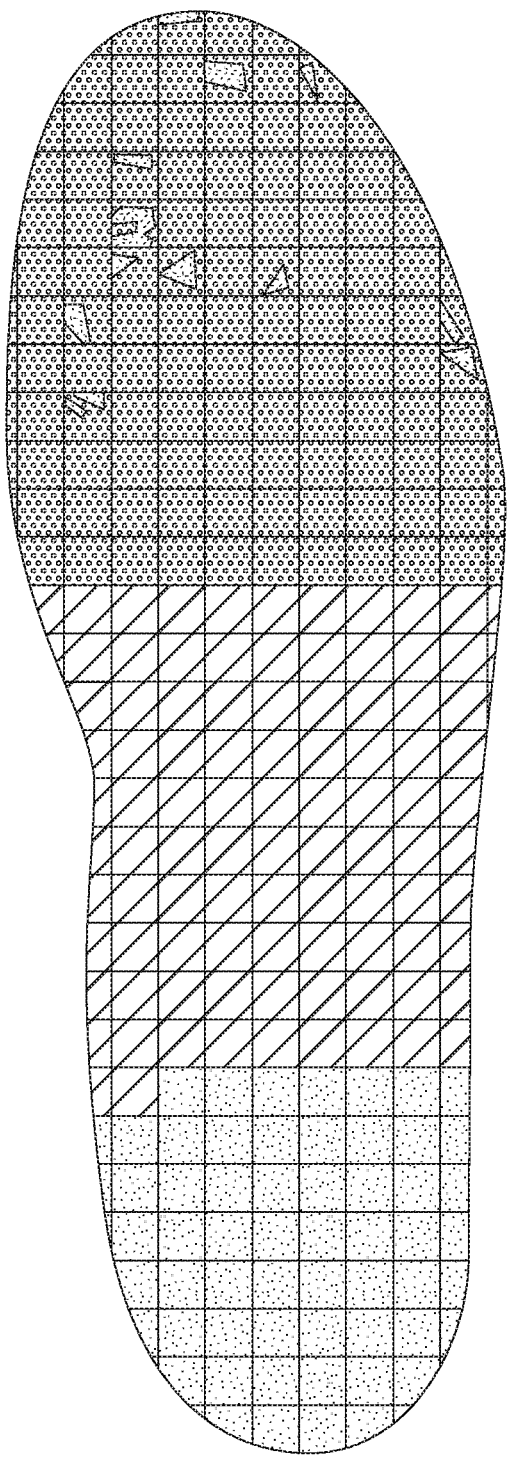
Figure 12:
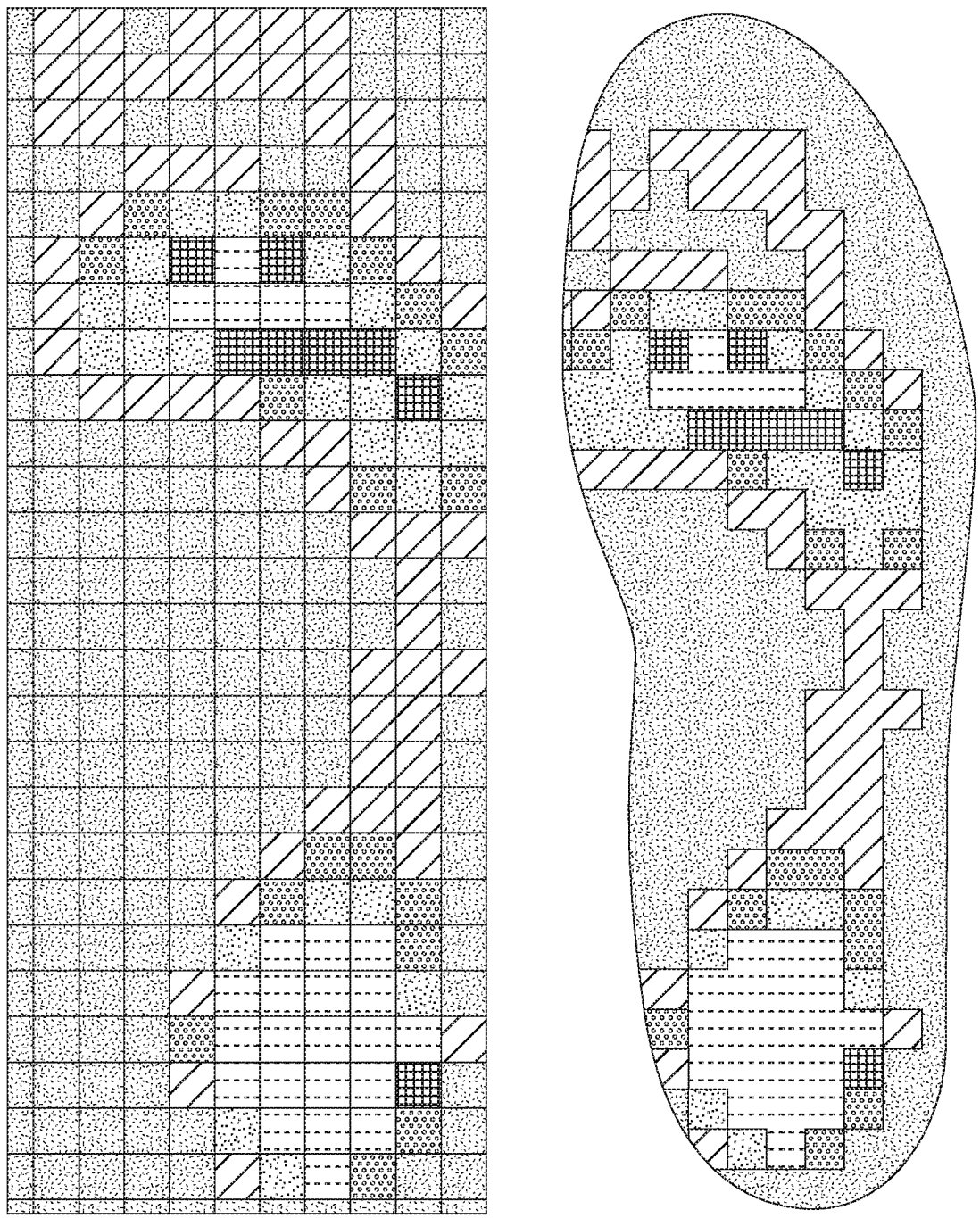

Turning now to FIGS. 10 through 16, an exemplary process flows as follows. In FIG. 10, a pressure map of a person's foot is received as a .png file. A "shell" form is imported in FIG. 11. In FIG. 12, the .png file of FIG. 10 is then imported and applied in the shell of FIG. 11.

Figure 13:
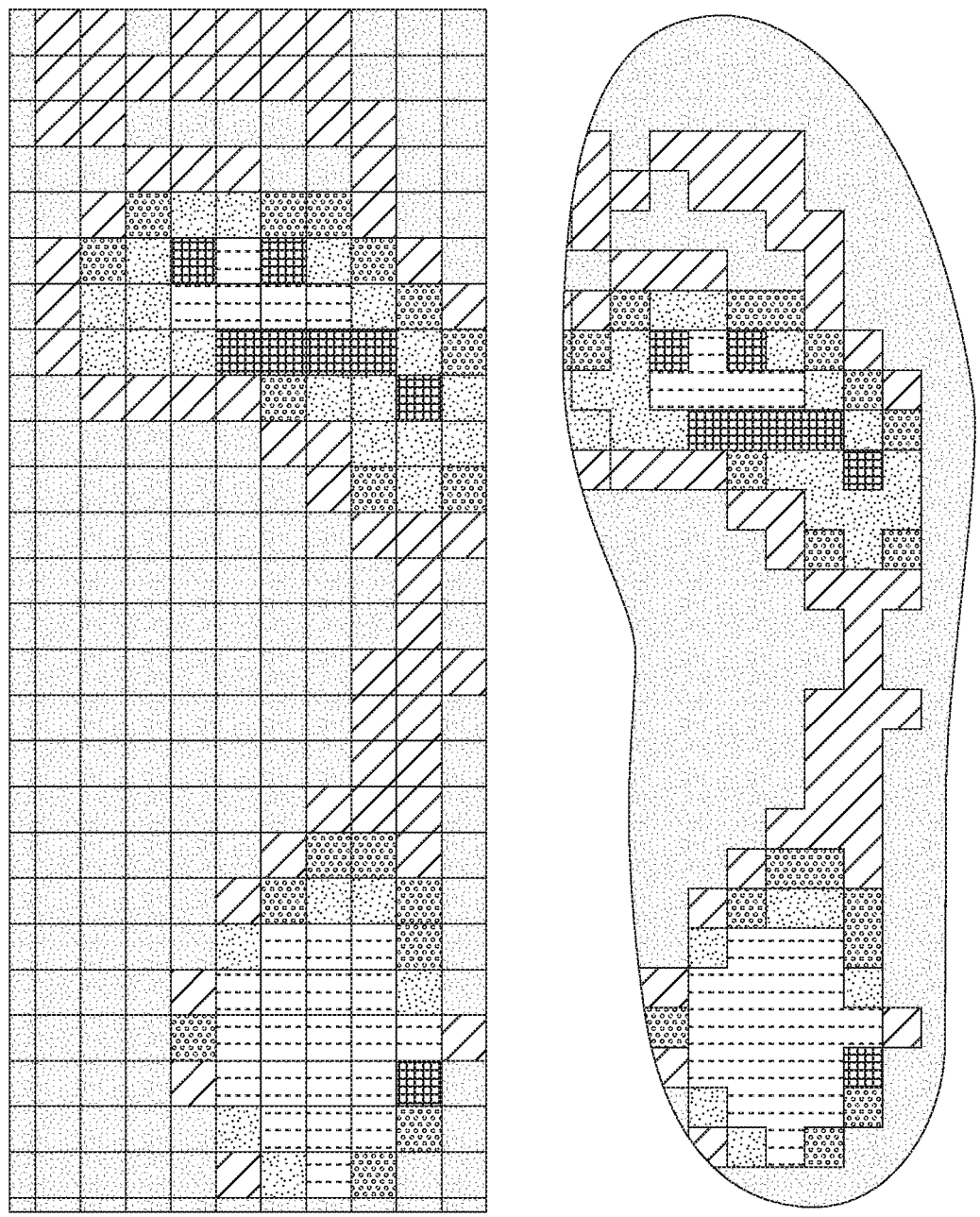
Figures 15, 16:
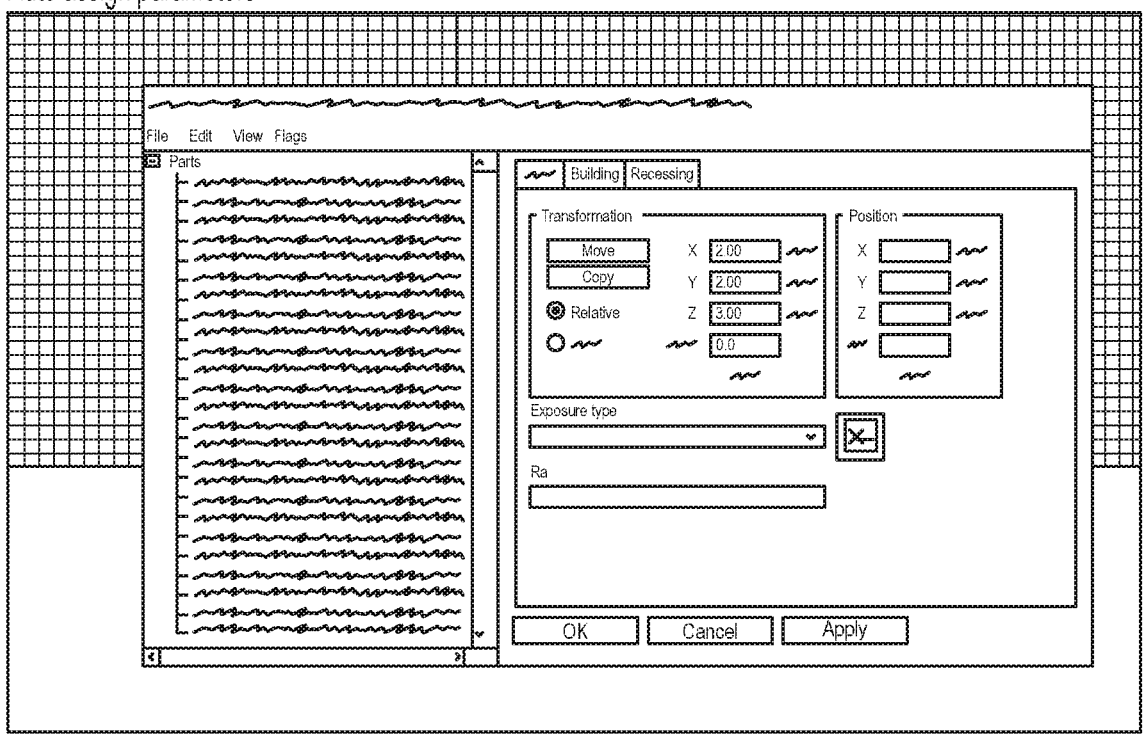

Structural elements are then drawn from the element database corresponding to the applied .png data in the shell, in FIG. 13. That structure is then output as a series of .stl files, in FIG. 14, and then slice files .sli for the particular powder bed fusion machine being used: an EOS P7 machine. Parameters are assigned in FIG. 16, and the build is ready.

Figure 17:
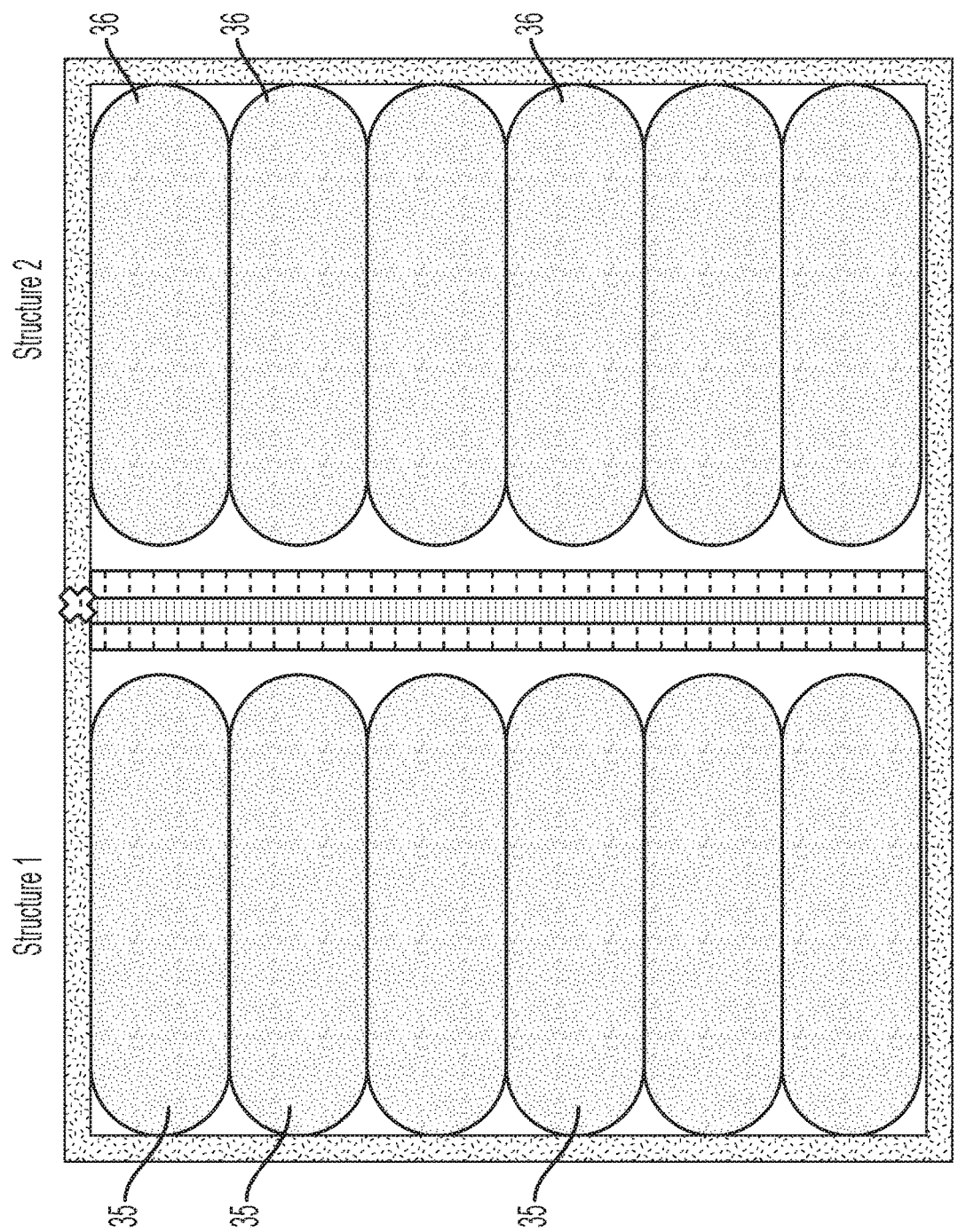

A difficulty that was overcome in this process for making a product with differing adjacent or contiguous areas having various hardness and compression responses, was how to meld the different areas so as to avoid delamination in the product, i.e., the areas coming apart in use. FIG. 17 illustrates the problem schematically.

On one side is a first Structure 1 made up of elements 35. Adjacent is another side or area Structure 2 made up of a different structural element 36. When using a laser beam with "standard" offsets, the area in the middle, denoted by the "x", would form a "gap" between the adjacent elements being generated, at most weakly binding them along the gap.

What the inventors did to overcome this problem is shown in FIG. 18. The laser beam offset was set to zero. This resulted in the creation of an overlap beam application for the two adjacent areas, shown at 40. The edges of the two different structural elements 35, 36 were thereby fused along this contiguous region, providing a smooth transition and strong merger.

While there has been described herein the principles of the invention, it is to be understood by those skilled in the art that this description is made only by way of example and not as a limitation to the scope of the invention. Accordingly, it is intended by the appended claims, to cover all modifications of the invention which fall within the true spirit and scope of the invention.

What is claimed is:

1. A method for making an article for footwear, the method comprising the steps of:
   obtaining data from measurement of pressures across an area of a subject foot;
   corresponding the data to a two-dimensional pressure map of a model of an article for footwear and identifying pressure-point locations of the subject foot on the model;
   determining pressure values for the identified pressure-point locations within the pressure map;

providing for each of the pressure values a compression unit structure corresponding to each respective pressure value;

assigning a respective structure to a position on the model according to the identified pressure point locations and the pressure values corresponding to the locations; and forming the article of footwear by generating the assigned respective structures in an integrated one-piece construct through layerwise build up in an additive manufacture system, where the build up includes a process that forms a joinder in an interface between adjacent contiguous structures which differ in geometry from one another so as to bond the contiguous structures together across the interface, where the joinder is created by providing a zero laser beam offset to create an overlap between adjacent contiguous areas of differing structures.

2. A method for making an article for application to a person's body, the method comprising the steps of:

obtaining data from measurement of pressures across an area of the person's body;

corresponding the data to a two-dimensional pressure map of a model of an article for application to the area of the person's body and identifying pressure-point locations of the subject area on the model;

determining pressure values for the identified pressure-point locations within the pressure map;

providing for each of the pressure values a compression unit structure corresponding to each respective pressure value;

assigning a respective structure to a position on the model according to the identified pressure point locations and the pressure values corresponding to the locations; and forming the article by generating the assigned respective structures in an integrated one-piece construct through layerwise build up in an additive manufacture system, where the build up includes a process that forms a joinder in an interface between adjacent contiguous structures which differ in geometry from one another so as to bond the contiguous structures together across the interface, and the joinder is created by providing a zero laser beam offset to create an overlap between adjacent contiguous areas of differing structures.

3. In a process for making objects using additive manufacture where an object is made from a build material which is solidified by application of a laser beam in successive layers which correspond to respective cross sections of the object to be built, wherein the improvement comprises:

generating elemental structures which have differing characteristics of hardness and flexibility;

assigning respective elemental structures to areas of a layer which is being built to provide groupings of same elemental structures in areas which then differ in characteristics of hardness and flexibility depending upon the elemental structures assigned to the area, at least some of the areas having different characteristics of hardness and flexibility and being adjacent and contiguous in a layer; and forming a joinder in an interface region between adjacent contiguous elemental structures which differ from one another so as to bond the contiguous structures together across the interface region by the laser beam offset being set to zero, so as to yield an overlap beam application for the two adjacent contiguous areas in the interface region, and thereby fusing the adjacent contiguous structures along the interface region.

4. In a process for making objects using additive manufacture where an object is made from a build material which is solidified by application of a laser beam in successive layers which correspond to respective cross sections of the object to be built, wherein the improvement comprises:

generating elemental structures which have differing characteristics of hardness and flexibility;

assigning respective elemental structures to areas of a layer which is being built to provide groupings of same elemental structures in areas which then differ in characteristics of hardness and flexibility depending upon the elemental structures assigned to the area, at least some of the areas having different characteristics of hardness and flexibility and being adjacent and contiguous in a layer; and forming a joinder in an interface region between adjacent contiguous elemental structures which differ from one another so as to bond the contiguous structures together across the interface region by the laser beam in a single pass, where a first structural element is overlapped with a second structural element which is contiguous with the first structural element but is of a different characteristic of hardness and flexibility from that of the first structural element, so as to yield an overlap beam application for the two adjacent contiguous areas in the interface region, and thereby fusing the adjacent contiguous structures along the interface region.

* * * * *